United States Patent [19]

Wineholt et al.

[11] 4,278,616

[45] Jul. 14, 1981

[54] 4,4'-THIODIPHENOL-FORMALDEHYDE CONDENSATION PRODUCTS

[75] Inventors: Robert L. Wineholt, Wyomissing Hills; James F. Feeman, Wyomissing, both of Pa.

[73] Assignee: Crompton & Knowles Corp., New York, N.Y.

[21] Appl. No.: 25,011

[22] Filed: Mar. 29, 1979

[51] Int. Cl.³ .................. C07C 143/42; C07C 143/52; D06P 5/02

[52] U.S. Cl. ............................ 260/512 C; 260/512 R; 260/507 R

[58] Field of Search ............ 260/512 C, 512 R, 507 R

[56] References Cited

FOREIGN PATENT DOCUMENTS 2122710  1/1971  France ................................. 260/512 C
7308293  6/1972  Netherlands ......................... 260/512 C Primary Examiner—A. Siegel
Attorney, Agent, or Firm—William H. Elliott, Jr.

[57] ABSTRACT

This invention relates to new 4,4' thiodiphenolformaldehyde condensation products and to a method of making said condensation products.

9 Claims, No Drawings

4,4'-THIODIPHENOL-FORMALDEHYDE CONDENSATION PRODUCTS

The condensation products of this invention have the structure

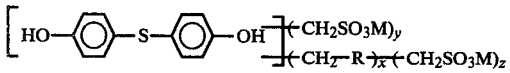

wherein R is a radical derived from a phenolic compound capable of reacting with formaldehyde; x is 1, 2, 3 or 4; y is 0, 1, 2 or 3; z is 0, 1, 2, 3 or 4; y+z is 1, 2, 3 or 4 and M is H, Na, K, Li, $NH_4$ or the mono, di or trialkanol amines having the structure $-N(R_3)_4$ where $R_3$ represents the same or different substituents selected from the following: $-H$, $-CH_2CH_2OH$, $-CH_2CH(OH)CH_3$ or $-CH_2CH_2OCH_2CH_2OH$.

The condensation products of this invention are useful as fixatives or agents for the aftertreatment of acid dyed polyamide textiles and when so used they enhance the wet-fastness of dyeings; hence another aspect of this invention is the use of these novel condensation products as fixatives for acid dyes on polyamide.

The condensation products of this invention are also useful as reserving agents to prevent polyamide fibers from being stained by direct dyes when polyamide fibers are present in a mixed fiber textile product containing both polyamide fibers and cellulosic fibers and the cellulosic component is being dyed with direct dyes.

The condensation products of this invention are made by reacting 1 mole of 4,4'-thiodiphenol (hereinafter sometimes designated as TDP) with about 1 to 4 moles formaldehyde in the presence of aqueous alkali, condensing the resulting reaction product with about ½ to 4 moles of a phenolic compound under strongly acid conditions and thereafter sulfomethylating the resulting condensation product by reacting it under neutral to alkaline conditions with sufficient formaldehyde-bisulfite adduct to make the condensation water soluble—i.e. usually about 1 to 4 moles formaldehydebisulfite adduct per mole of TDP.

An essential feature of the process involves completely dissolving the TDP in aqueous alkali (e.g. aqueous sodium hydroxide solution) before the addition of the formaldehyde and maintaining the reactants and reaction mass in a dissolved state until the reaction has been completed. This assures uniformity of methylolation.

The methylolation is carried out at elevated temperatures e.g. above about 50° C. and preferably between 80°–90° C. During methylolation the amount of alkali present should be sufficient to maintain the reactants and the resulting reaction products in solution even after cooling the reaction mass. Usually, this can be accomplished by carrying out the methylolation at a pH above 9.

For purposes of this invention the phenolic component can be provided by a phenolic compound capable of reacting with the methylolated TDP through a methylene bridge and provided that the phenolic is not of a size or does not include substituents that would preclude its water solubilization by the eventual introduction of 1 to 4 sulfomethyl groups per mole of TDP in the final product.

Especially suitable phenolic compounds include phenol, cresols, xylenols, catechol, resorcinol, hydroxybenzoic acids, naphthols, bisphenols, phenyl phenols, thiodiphenols.

About 1 to 4 moles of the phenolic compound should be condensed with 1 mole TDP-methylol derivative. Below 1 mole of the phenolic compound the ability of the condensation product to function as a fixative is significantly reduced.

The condensation reaction should be carried out at somewhat elevated temperatures (generally above about 50° C. but below 100° C.) and under strongly acidic conditions so as to insure methylene bridge formation between the TDP and the phenolic compound. Generally a pH less than 1 is sufficient and can be provided by any mineral acid and preferably by hydrochloric acid.

Preferably the product of this acid condensation should be completely redissolved in aqueous alkali before sulfomethylation with a formaldehyde-bisulfite adduct formed from an aqueous solution of sodium metabisulfite and formaldehyde. This insures uniformity and proper solubility of the final product by providing for uniform introduction of solubilizing sulfomethyl groups on carbon atoms ortho to phenolic hydroxyl groups in the condensation product. Thus good solubility is achieved with a minimum number of sulfomethyl groups, thereby assuring maximum effectiveness of the product.

The sulfomethylation is preferably carried out by prolonged reaction at elevated temperatures—e.g. by 12–24 hours at near the boil and under neutral or alkaline conditions but usually in the presence of sufficient alkali to keep the reaction mass in solution. After completion of the sulfomethylation the reaction mass is cooled and acidified. Preferably the mass is first cooled to about 50° and then rendered mildly acidic (e.g. a pH of about 5 to 6.5) by the addition of mineral acid—e.g. hydrochloric acid. On further cooling the sulfomethylated condensation product will precipitate and can be recovered by conventional methods.

It is preferable to employ sufficient bisulfite-adduct in the sulfomethylation step to insure reasonable solubility of the final product in cold water at customary dyeing liquor ratios. This level of sulfomethylation is achieved by the use of from 1 to 4 moles of adduct of each mole of TDP.

Where phenol, a cresol, a xylenol, catechol, resorcinol, or a hydroxy benzoic acid, is used as the phenolic compound in the condensation reaction the final sulfomethylated compound has the structure

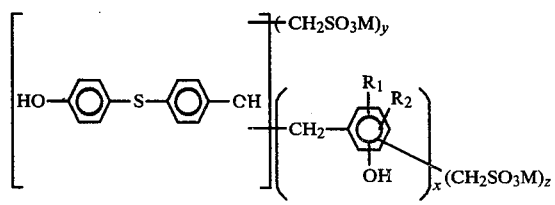

wherein M, x, y and z have the same meanings as heretofore given and $R_1$ is H, $CH_3$, OH or COOH and $R_2$ is H, $CH_3$ or OH.

Depending on the exact conditions under which the various reactions are carried out it is also believed possible that compounds having either of the following structure may be produced.

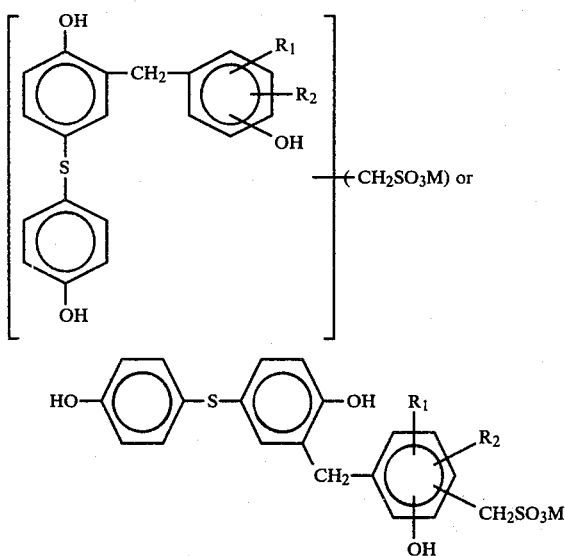

wherein M, $R_1$ and $R_2$ have the meanings heretofore given.

The sulfomethylated condensation products of this invention are useful as fixatives for acid dyes that have been applied to polyamide fibers such as nylon and enhance the wet fastness of such dyeings.

The fixative can be applied from the dye bath at the end of the dyeing cycle—or it can be applied from a fresh bath by exhaustion or by padding onto the dyed fabric in which case the dyed fabric is passed through an aqueous solution of the fixative, excess liquid is removed and the treated fabric dried. The amounts of fixative to be applied can vary within wide limits. Applying from 0.1% to 2% of the condensation product based on the weight of the fabric undergoing treatment will usually serve to provide a concentration sufficient to significantly enhance the wet-fastness of dyeings of acid dyes on nylon and for most purposes the use of about ½% of the fixative will be satisfactory.

The condensation products prepared from phenol are outstanding both as fixatives for acid dyes on polyamide fiber and as reserving agents. As fixatives they are superior to any presently used fixative except the widely used and much more expensive tannic acid-tartar emetic after treatments; moreover, they do not discolor on exposure to light thereby overcoming a defect of the tannic acid-tartar emetic and many other commonly used after treatments.

The sulfomethylated condensation products of this invention are also useful resists or reserving agents (i.e. substances which repel or resist dyes and prevent their fixation on material) to prevent direct dyes from staining polyamides such as nylon. Thus in cases where a mixed fiber textile formed of nylon and a cellulosic fiber component (cotton, jute, linen, regenerated cellulose and the like) is subjected to conventional dyeing operation with direct dyes, the nylon can be reserved by carrying out the dyeing in the presence of the water soluble sulfomethylated condensation products of this invention.

The reserving agent can be applied to the textile undergoing treatment in a separate wet processing operation before dyeing with the direct dye. Applying from about ¼% to about 4% of the condensation product based on the weight of the textile undergoing treatment will usually serve to provide a suitable concentration of the resist to prevent to a significant degree the polyamide fibers of a mixed fiber textile from being dyed by the direct dye, and for most purposes, the use of about 1% of the reserving agent will provide adequate resist.

The following examples serve to illustrate the invention and in these examples, unless otherwise stated, the parts expressed are parts by weight and temperatures are expressed on the centigrade scale.

EXAMPLE 1

To a mixture of 30 ml. of water and 9.0 g. of 50% sodium hydroxide at 65° C., was added 21.8 g. of 4,4'-thiodiphenol. After the thiodiphenol dissolved, 8.1 g. of 37% formaldehyde was added. The mixture was heated at 85° C. for two hours and then cooled at 70° C. At 70° C., 9.4 g. of phenol was added, followed by 11.5 ml. of concentrated hydrochloric acid. The mixture was heated at 85° C. for two hours.

Formaldehyde-bisulfite adduct was prepared as follows: to a solution of 11.0 g. of sodium metabisulfite in 20 ml. of water, was added 8.1 g. of 37% formaldehyde. The mixture was stirred for ten minutes.

The condensation slurry was made basic by addition of 16.0 g. of 50% sodium hydroxide and the formaldehyde-bisulfite adduct was added to the slurry. The mixture was heated at 90°–95° C. for eighteen hours. After cooling to 50° C., the pH of the solution was brought to 6.0–6.5 with concentrated hydrochloric acid. The mixture was cooled to 30° C. and a gum precipitated which may have the following structure:

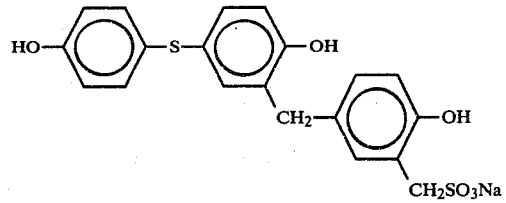

The supernatant liquid was decanted from the gum. The gum was dissolved in sufficient water to bring the solids content of the solution to 15%±1%. The solution was clarified by filtration and the solution used as an acid dye fixative or reserve agent for nylon as described in Examples 2a and 2b.

EXAMPLE 2a

Type 66 nylon tricot fabric was dyed at 4% o.w.f. (i.e.—on weight of fabric) with C.I. Acid Blue 113.

A stock fixative solution was prepared by dissolving 5 g. of the 15% (solids) solution from Example 1 in 500 ml. of water.

2.5 g. pieces of the dyed nylon fabric were set in small Launderometer cans each of which contained 50 ml. of soft water at 100° F. Varying amounts of the stock fixative solution were added to each of the cans as follows:

| Can # | fixative Ml Stock solution | fixative % o.w.f. |
| --- | --- | --- |
| 1 (Control) | 0 | 0 |
| 2 | 10 | 4 |
| 3 | 14 | 5.6 |
| 4 | 20 | 8.0 |

| Can # | fixative Ml Stock solution | fixative % o.w.f. |
|---|---|---|
| 5 | 40 | 16.0 | and the total volume in each can was brought to 100 ml. The temperature was raised to 160° F. and held for 30 minutes. The cans were cooled and the treated fabrics removed, rinsed and dried.

The thus treated fabrics were subjected to a washfastness test by a modified AATCC test method 36-1961 (II)—i.e. the fabrics were washed at 160° F. rather than at 120° F. as called for by the test method.

The wash tested fabrics were evaluated (using the usual AATCC numerical ratings running from 5 to 1 in which 5 represents no or negligible staining, 4 represents slight staining and 3 represents noticable staining of the wash test multifiber) as follows:

| Fabric from Can # | Fixative % o.w.f. | Stain rating of nylon component of the Washtest multifiber |
|---|---|---|
| 1 | 0 | 3 |
| 2 | 4 | 4− |
| 3 | 5.6 | 4−5 |
| 4 | 8.0 | 4−5 |
| 5 | 16.0 | 5− |

EXAMPLE 2b

A stock resist solution was prepared by dissolving 5 g. of the 15% (solids) solution from Example 1 in 500 ml water.

Fabric samples weighing 10 g. each were prepared by stapling a 5 g. cutting of spun rayon challis to a 5 g. cutting of woven nylon and were set in small size Launderometer cans each of which contained 100 ml soft water and 25 ml C.I. Direct Red 80 stock solution (1 g. dye in 500 ml water). Various amounts of the stock resist solution were added to each of the cans as follows:

| Can # | Resist ml Stock Solution | Resist % o.w.f. |
|---|---|---|
| 1 | 0 | 0 |
| 2 | 5 | 1 |
| 3 | 15 | 3 |
| 4 | 30 | 6 |

To each can was added: 1 ml 10% ammonium sulfate solution, 10 ml 10% Glauber's salt solution and water to bring the volume to 200 ml.

The cans were placed in a Launderometer, the temperature raised to 205° F. and held at that temperature for 1 hour. The treated fabrics were removed, rinsed in warm water and dried.

The nylon component of the sample from Can #1 was stained by the red dye whereas the samples from Cans #2, #3 and #4 that had been treated with the resist were only slightly stained and the degree of staining fell off as concentration of the resist increased.

Table 1 below lists the mole ratio of 4,4′-thiodiphenol, 37% formaldehyde, phenol, and formaldehyde-bisulfite adduct used to produce other materials of the invention.

TABLE 1

| Ex. No. | 4,4′-thiodiphenol | formaldehyde | phenol | formaldehyde-bisulfite adduct |
|---|---|---|---|---|
| 3 | 1 | 0.8 | 1 | 1.1 |
| 4 | 1 | 0.6 | 1 | 1.1 |
| 5 | 1 | 1.2 | 1 | 1.1 |
| 6 | 1 | 1.4 | 1 | 1.1 |
| 7 | 1 | 1 | 0.8 | 1.1 |
| 8 | 1 | 1 | 0.6 | 1.1 |
| 9 | 2 | 2 | 1 | 2.2 |
| 10 | 3 | 3 | 1 | 3.3 |
| 11 | 1 | 2 | 2 | 2.2 |

EXAMPLE 12

As in Example 1, the formaldehyde-thiodiphenol condensation was repeated. Phenol was replaced by 11 g. resorcinol. After sulfomethylation with formaldehyde-bisulfite, a solution was obtained as in Example 1. The solution obtained fixed acid dyes on polyamide fibers and provided outstanding wet-fastness; however a tendency to discolor on exposure to light limits its use to dyeings having dark shades.

EXAMPLE 13

The 4,4′-Thiodiphenol-formaldehyde condensation was repeated as in Example 1 using 2-Naphthol (14.4 g.) to replace the 9.4 g. phenol. Sulfomethylation of the thiodiphenol-formaldehyde-betanaphthol condensation furnished a product which fixed acid dyes on polyamide fibers to about the same extent as the compound of Example 1.

We claim:

1. A compound having the structure

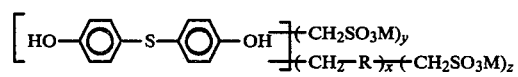

wherein R is a phenolic radical selected from the group consisting of phenol, a cresol, a xylenol, catechol, resorcinol, a hydroxy-benzoic acid, a napthol, a bisphenol, a phenyl-phenol, and thiodiphenol; x is 1, 2, 3 or 4; y is 0, 1, 2 or 3, z is 0, 1, 2, 3 or 4 and y+z is 1, 2, 3 or 4 and M is H, Na, K, Li, NH$_4$ or a mono, di or tri alkanol ammonium ion.

2. A compound having the structure

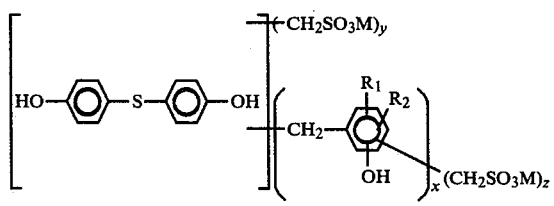

wherein M, x, Y and z have the same meanings as in claim 1; R$_1$ is H, CH$_3$, OH or COOH, and R$_2$ is H, CH$_3$, or OH.

3. A compound having the structure

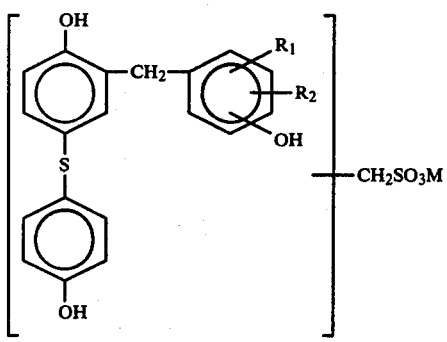

wherein M, $R_1$ and $R_2$ have the same meaning as in claim 2.

4. A compound having the structure

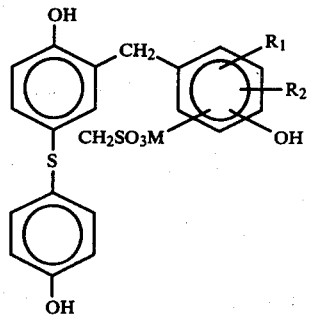

wherein M=H, Na, K or Li; $R_1$=H, $CH_3$, OH or COOH; and $R_2$=H, $CH_3$ or OH.

5. A compound according to claim 1 or 2 wherein R is phenol.

6. A compound according to any of claims 2, 3 or 4 wherein M is Na.

7. A compound according to any of claims 2, 3 or 4 wherein $R_2$ is H.

8. A compound according to any of claims 2, 3 or 4 wherein $R_1$ and $R_2$ are H.

9. A compound according to any of claims 2, 3 or 4 wherein $R_1$ and $R_2$ are H and M is Na.

* * * * *